United States Patent [19]
Chorvat

[11] 4,223,136
[45] Sep. 16, 1980

[54] 2,3-DIHYDRO-3-OXO-5H-PYRIDO[3,4-b][1,4]-BENZOTHIAZINE-4-CARBONITRILES

[75] Inventor: Robert J. Chorvat, Arlington Heights, Ill.

[73] Assignee: G. D. Searle & Co., Skokie, Ill.

[21] Appl. No.: 63,607

[22] Filed: Aug. 3, 1979

[51] Int. Cl.$^2$ ............................................. C07D 513/14
[52] U.S. Cl. ..................................................... 544/34
[58] Field of Search ......................................... 544/34

[56] References Cited

U.S. PATENT DOCUMENTS 3,389,136   6/1968   Clarke ..................................... 544/34

Primary Examiner—John M. Ford
Attorney, Agent, or Firm—James R. Henes

[57] ABSTRACT

2,3-dihydro-3-oxo-5H-pyrido[3,4-b][1,4]-benzothiazine-4-carbonitriles having anticonvulsant and anxiolytic activity and their preparation from 2H-1,4-benzothiazin-3-(4H)-ones are disclosed.

23 Claims, No Drawings

2,3-DIHYDRO-3-OXO-5H-PYRIDO[3,4-b][1,4]-BENZOTHIAZINE-4-CARBONITRILES

This invention relates to 2,3-dihydro-3-oxo-5H-pyrido[3,4-b][1,4]benzothiazine-4-carbonitriles and processes for the preparation thereof. More particularly, this invention provides (1) new, useful, and unobvious chemical compounds of the formula

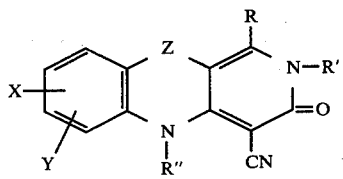

wherein R represents hydrogen or a straight-chain alkyl containing 1 to 3 carbon atoms; R' and R" each represent hydrogen or straight-chain or branched-chain alkyl containing 1 to 3 carbon atoms; X represents hydrogen, fluorine, chlorine, bromine, nitro, or alkoxy containing 1 to 4 carbon atoms; when X is other than alkoxy, Y represents hydrogen, and when X is alkoxy, Y is hydrogen or the same alkoxy; Z represents sulfur, sulfinyl, or sulfonyl; and X can additionally represent amino when Z represents sulfur; and (2) acid addition salts of compounds of the above formula wherein X represents amino.

Suitable alkyls represented by R include methyl, ethyl and n-propyl. Suitable alkyls represented by R' or R" include methyl, ethyl, 1-methylethyl and n-propyl. When one of R, R' or R" is alkyl, preferably the alkyl is methyl. Suitable alkoxys represented by X or Y include methoxy, ethoxy and straight-chain or branched-chain propoxy or butoxy. When X and Y are alkoxy, preferably the alkoxy is methoxy. Suitable amino addition salts include those made from acids listed hereinbelow and in preferred embodiments include only those free of toxic side effects.

Equivalent to the foregoing compounds—including salts—for the purposes of this invention are solvates thereof in which pharmacologically insignificant amounts of solvent are present.

The compounds to which this invention relates are useful because of their valuable pharmacological properties. Thus, for example, they are anticonvulsant and anxiolytic.

The anticonvulsant utility of the instant compounds is evident from the results of a standardized test for their capacity to prevent clonic convulsions induced in mice by pentylenetetrazole. The procedure, a modification of one described by Chen et al. in Proc. Soc. Exp. Biol. and Med., 87, 337 (1954), is as follows: A selected dose (commonly but not invariably 100 mg/kg in the first instance) of the compound to be tested, suspended in 10 ml of a vehicle consisting of approximately 9.8 ml of physiological saline intimately mixed with 0.1 ml of propylene glycol and 0.1 ml of polysorbate 80, is administered intragastrically (IG) or intraperitoneally (IP) to each of a group of 10 male Crl:COB CD-1(ICR)BR mice weighing 18–28 g apiece. After a selected interval of time (¼, ½, 1, 3, 6, or 24 hr.), each mouse is challenged by intravenous infusion of 35 mg/kg of pentylenetetrazole (sufficient to induce clonic convulsions in control animals) administered as a 0.35% aqueous solution at a rate of approximately 0.1 ml/sec. A compound is considered anticonvulsant at the selected dose if, after the selected time, clonic convulsions are prevented in at least 20% of the animals challenged. The products of Examples 2 and 12D hereinafter (namely 2,3-dihydro-3-oxo-5H-pyrido[3,4-b][1,4]benzothiazine-4-carbonitrile 10-oxide and 7-chloro-2,3-dihydro-3-oxo-5H-pyrido[3,4-b][1,4]benzothiazine-4-carbonitrile) were anticonvulsant in this test 1 hr. after IP administration of 25 and 32 mg/kg, respectively.

The anxiolytic utility of the instant compounds is evident from the results of a standardized test, adapted from that described by Vogel et al. in Psychopharmacologia, 21, 1 (1971), whereby the capacity of a compound to increase punished response behavior in rats is evaluated. The products of Examples 2 and 12D hereinafter increased such behavior in this test at 18 and 32 mg/kg IP, respectively.

Those skilled in the art will appreciate that the characterizing pharmacological responses to embodiments of this invention specified above are intended merely for purposes of illustration and, accordingly, are not to be construed as either delimiting or exclusionary.

For therapeutic purposes, the compounds of this invention are ordinarily combined with one or more adjuvants appropriate to the indicated route of administration. If per os, they may be admixed with lactose, sucrose, starch powder, cellulose esters of alkanoic acids, cellulose alkyl ethers, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and thus tableted or encapsulated for convenient administration; alternatively, they may be dissolved or suspended in water or a comparably innocuous liquid. Parenteral administration may be effected via sterile fluid admixture with water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art; see, for example, F. W. Martin et al., "Remington's Pharmaceutical Sciences," 14 Ed., Merck Publishing Company, Eaton, Pa. 1965.

Appropriate dosages, in any given instance of course depend upon the nature and severity of the condition treated, the route of administration, and the species of mammal involved, including its size and any individual idiosyncrasies which obtain.

Compounds of this invention when X is not an amino group can be prepared as follows: A 2H-1,4-benzothiazin-3-(4H)-one of the formula

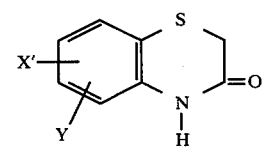

wherein X' is hydrogen, fluorine, chlorine, bromine, nitro or an alkoxy containing 1 to 4 carbon atoms and, when X' is other than alkoxy, Y is hydrogen and, when X' is alkoxy, Y is hydrogen or the same alkoxy, is heated in 1,4-dioxane with diphosphorus pentasulfide to obtain a corresponding thione comprehended by the formula

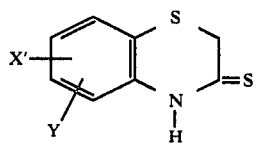

Suitable alkoxys represented by X' include methoxy, ethoxy, and straight-chain or branched-chain propoxy or butoxy. Preferably when X' is an alkoxy, the alkoxy is methoxy.

Such a thione is contacted with sodium hydride in tetrahydrofuran under nitrogen, and the resultant sodio derivative is contacted in situ with iodomethane to obtain a corresponding 3-methylthio-2H-1,4-benzothiazine comprehended by the formula

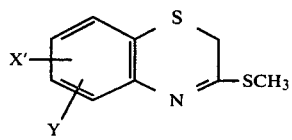

Such a methylthio compound is heated in N,N-dimethylformamide under nitrogen with the sodio derivative of 2-cyanoacetamide prepared in situ by contacting the amide with sodium hydride, whereby a corresponding 2-cyano-2-[2,3-dihydro-4H-benzothiazin-3-ylidene]acetamide is obtained which is comprehended by the formula

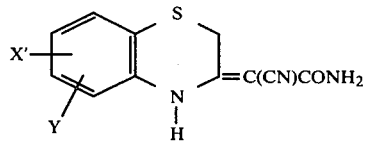

Such an amide is contacted in N,N-dimethylformamide under nitrogen with a dimethyl or diethyl ketal of the formula

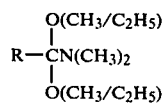

wherein R is hydrogen, methyl, ethyl or n-propyl, and the resultant adduct is cyclized by heating to obtain a corresponding 2,3-dihydro-3-oxo-5H-pyrido[3,4-b][1,4]benzothiazine-4-carbonitrile comprehended by the formula

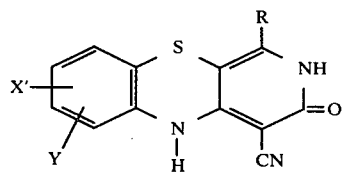

Compounds of this invention when X is an amino group can be prepared as follows: a 2,3-dihydro-3-oxo-5H-pyrido[3,4-b][1,4]benzothiazine-4-carbonitrile of the formula

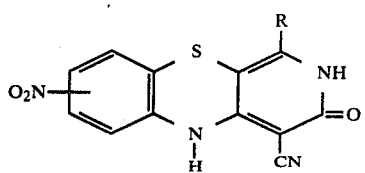

is heated with stannous chloride dihydrate in a mixture of hydrochloric and acetic acids to obtain a corresponding amino compound comprehended by the formula

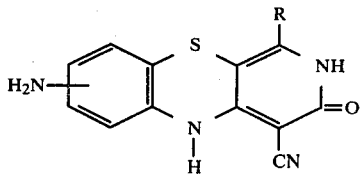

A 2,3-dihydro-3-oxo-5H-pyrido[3,4-b][1,4]benzothiazine-4-carbonitrile of the formula

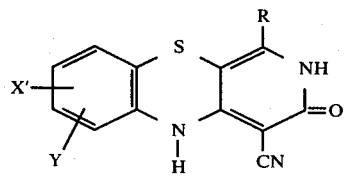

is contacted in N,N-dimethylformamide with an iodoalkane in the presence of potassium carbonate to obtain a corresponding 2-alkyl-2,3-dihydro-3-oxo-5H-pyrido[3,4-b][1,4]benzothiazine-4-carbonitrile comprehended by the formula

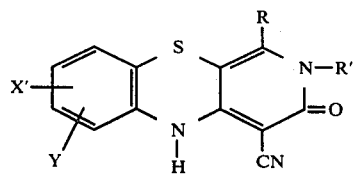

wherein R' represents alkyl containing 1 to 3 carbon atoms as defined above, and which in turn is heated in N,N-dimethylformamide with an iodoalkane in the presence of potassium carbonate to obtain a corresponding 2,5-dialkyl-2,3-dihydro-3-oxo-5H-pyrido[3,4-b][1,4]benzothiazine-4-carbonitrile comprehended by the formula

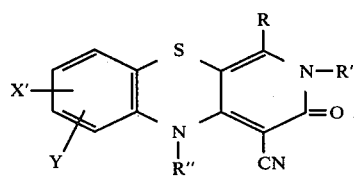

wherein R' and R" represent alkyls each containing 1 to 3 carbon atoms as defined above.

Such a 2,5-dialkyl compound of the above-noted 2,3-dihydro-3-oxo-5H-pyrido[3,4-b][1,4]benzothiazine-4-carbonitrile is contacted with ethaneperoxoic acid in acetic acid to obtain a 10-oxide comprehended by the formula

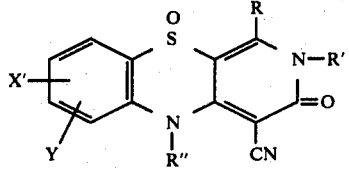

and such a 10-oxide or its immediate precursor is heated with ethaneperoxoic acid in acetic acid to obtain a corresponding 10,10-dioxide comprehended by the formula

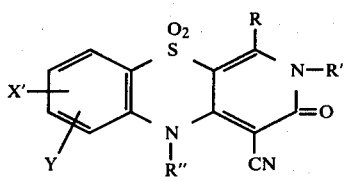

Alternatively, a 2,3-dihydro-3-oxo-5H-pyrido[3,4-b][1,4]benzothiazine-4-carbonitrile of the formula

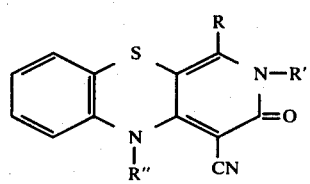

is (1) heated with bromine in a mixture of carbon tetrachloride and acetic acid to obtain a corresponding 8-bromo compound comprehended by the formula

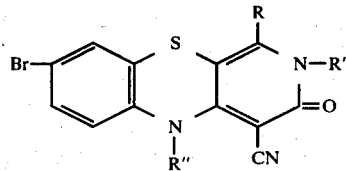

or (2) contacted with a cold mixture of nitric and sulfuric acids to obtain a corresponding 8-nitro 10-oxide comprehended by the formula

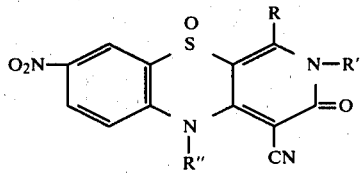

which in turn is heated with triphenylphosphine in a mixture of tetrachloromethane and acetonitrile to obtain a corresponding 10-desoxidic compound comprehended by the formula

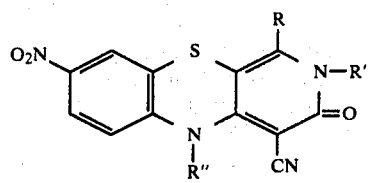

which is then heated with stannous chloride dihydrate in a mixture of hydrochloric and acetic acids to obtain—upon neutralization—a corresponding 8-amino 10-desoxidic compound comprehended by the formula

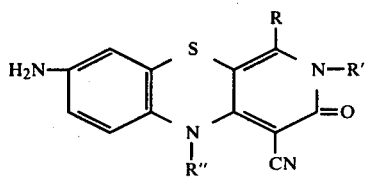

Finally, an acid addition salt of the invention when X is amino is obtained by contacting—ordinarily in a solvent medium—an amino compound of the formula

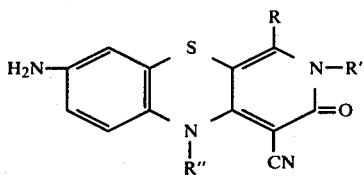

with an inorganic or strong organic acid such as hydrochloric, hydrobromic, hydriodic, nitric, phosphoric, sulfuric or the methyl or ethyl ester thereof, sulfamic, benzenesulfonic, methylbenzenesulfonic, acetic, 2-hydroxypropanoic, 3-phenyl-2-propanoic, butanedioic, 2,3-dihydroxybutanedioic, 2-butenedioic, 2-hydroxy-1,2,3-propanetricarboxylic, gluconic, ascorbic, benzoic, or the like, the relative amount of amino compound contacted being determined by the basicity of the acid and the stoichiometry elected where options are presented. Throughout the foregoing preparative disclosure, R, R', R", X, X', Y and Z retain the meanings originally assigned, except where otherwise indicated.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade and relative amounts of materials in part by weight, except as otherwise noted.

EXAMPLE 1

A. To 17 parts of sodium hydride in 1500 parts of tetrahydrofuran at room temperature under nitrogen is added, portionwise with stirring during approximately 15 minutes, 90 parts of 2H-1,4-benzothiazine-3(4H)-thione [J. Med. Chem. 12, 290 (1969)]. After the addition is complete, stirring under nitrogen is continued for 10 minutes, whereupon a solution of 85 parts of iodomethane in 70 parts of tetrahydrofuran is rapidly stirred in and stirring continued thereafter for a still further 15 minutes. Removal of solvent by vacuum distillation under nitrogen affords 3-methylthio-2H-1,4-benzothiazine as the residue. Since the product is subject to spontaneous hydrolytic decomposition, it is not usually isolated for the purposes of this invention but instead is employed as the solution in tetrahydrofuran preparable via the foregoing procedure.

B. To 18 parts of sodium hydride in 1100 parts of N,N-dimethylformamide at room temperature under nitrogen is added, portionwise with stirring during approximately 15 minutes, 63 parts of 2-cyanoacetamide. After the addition is complete, stirring under nitrogen is continued for 30 minutes, whereupon a solution of 97 parts of 3-methylthio-2H-1,4-benzothiazine in 1400 parts of tetrahydrofuran is stirred in during 10 minutes and the resultant mixture heated to, and stirred at, 70° for 16 hours. The mixture thus obtained is cooled to room temperature, then consecutively diluted with 750 parts of water and adjusted to a pH of approximately 7.5 with 5% hydrochloric acid. The precipitate which forms is filtered off, dried in air, and recrystallized from aqueous N,N-dimethylformamide to give 2-cyano-2-(2,3-dihydro-4H-benzothiazin-3-ylidene)acetamide melting at approximately 267°-260° with decomposition.

C. A mixture of 77 parts of 2-cyano-2-(2,3-dihydro-4H-benzothiazin-3-ylidene)acetamide, 57 parts of 1,1-dimethoxy-N,N-dimethylmethanamine, and 1425 parts of N,N-dimethylformamide is stirred under nitrogen until solution occurs, then heated at 145° under reflux for 6 hours, and finally allowed to cool to room temperature overnight. The precipitate which forms is filtered out and dried in vacuo. The yellow shiny needles of 2,3-dihydro-3-oxo-5H-pyrido[3,4-b][1,4]benzothiazine-4-carbonitrile thus isolated melts above 305°.

EXAMPLE 2

A mixture of 10 parts of 2,3-dihydro-3-oxo-5H-pyrido[3,4-b][1,4]benzothiazine-4-carbonitrile, 28 parts of ethaneperoxoic acid, and 242 parts of acetic acid is stirred at room temperature for 80 minutes, during which the color changes from bright yellow to pale yellow. Insoluble solids are thereupon filtered out, washed with methanol, and dried in vacuo. The product thus isolated is 2,3-dihydro-3-oxo-5H-pyrido[3,4-b][1,4]benzothiazine-4-carbonitrile 10-oxide.

EXAMPLE 3

A mixture of 3 parts of 2,3-dihydro-3-oxo-5H-pyrido[3,4-b][1,4]benzothiazine-4-carbonitrile, 56 parts of ethaneperoxoic acid, and 63 parts of acetic acid is stirred and heated at approximately 95° for 8 hours, then cooled to room temperature. Insoluble solids are filtered out, washed with methanol, dried in vacuo, and recrystallized from N,N-dimethylformamide to give 2,3-dihydro-3-oxo-5H-pyrido[3,4-b][1,4]benzothiazine-4-carbonitrile 10,10-dioxide melting above 300°.

EXAMPLE 4

A. A mixture of 24 parts of 2-cyano-2-(2,3-dihydro-4H-benzothiazin-3-ylidene)acetamide, 30 parts of 1,1-dimethoxy-N,N-dimethylethanamine, and 475 parts of N,N-dimethylformamide is stirred and heated at approximately 95° for 45 minutes, then cooled to room temperature and thereupon partitioned between trichloromethane and water. The trichloromethane phase is washed with a saturated aqueous solution of sodium chloride, dried over anhydrous sodium sulfate, and stripped of solvent by vacuum distillation. The residue, upon trituration with a mixture of methanol and 1,1'-oxybisethane, affords 2-cyano-2-(2,3-dihydro-4H-benzothiazin-3-ylidene)-N-[(1-dimethylamino)-ethylidene]acetamide as a crystalline solid which is isolated by filtration and dried in vacuo.

B. A mixture of 10 parts of 2-cyano-2-(2,3-dihydro-4H-benzothiazin-3-ylidene)-N-[(dimethylamino)ethylidene]-acetamide and 95 parts of N,N-dimethylformamide is heated at the boiling point under reflux for 5¾ hours, then concentrated to the point of incipient precipitation by distillation under nitrogen in vacuo. When precipitation is complete, insoluble solids are filtered out and dried in vacuo. The yellow crystalline product thus isolated is 2,3-dihydro-1-methyl-3-oxo-5H-pyrido[3,4-b][1,4]benzothiazine-4-carbonitrile.

EXAMPLE 5

A mixture of 24 parts of 2,3-dihydro-3-oxo-5H-pyrido[3,4-b][1,4]benzothiazine-4-carbonitrile, 14 parts of iodomethane and 14 parts of potassium carbonate is stirred at room temperature for 2¼ hours, then diluted with 2 volumes of water. The precipitate which forms is filtered out, dried in vacuo, and recrystallized from acetonitrile to give yellow needles of 2,3-dihydro-2-methyl-3-oxo-5H-pyrido[3,4-b][1,4]benzothiazine-4-carbonitrile melting at 292°-295° with decomposition.

EXAMPLE 6

Substitution of 10 parts of 2,3-dihydro-2-methyl-3-oxo-5H-pyrido[3,4-b][1,4]benzothiazine-4-carbonitrile for the 2,3-dihydro-3-oxo-5H-pyrido[3,4-b][1,4]-benzothiazine-4-carbonitrile called for in Example 2 affords, by the procedure there detailed, 2,3-dihydro-2-methyl-3oxo-5H-pyrido[3,4 -b][1,4]benzothiazine-4-carbonitrile 10-oxide.

EXAMPLE 7

Substitution of 18 parts of 1-iodo-2-methylpropane for the iodomethane called for in Example 5 affords, by the procedure there detailed, 2,3-dihydro-2-(2-methylpropyl)-3-oxo-5H-pyrido[3,4-b][1,4]benzothiazine-4carbonitrile.

EXAMPLE 8

Substitution of 10 parts of 2,3-dihydro-2-(2-methylpropyl)-3-oxo-5H-pyrido[3,4-b][1,4]benzothiazine-4-carbonitrile for the 2,3-dihydro-3-oxo-5H-pyrido[3,4-b]-[1,4]benzothiazine-4-carbonitrile called for in Example 2 affords, by the procedure there detailed, 2,3-dihydro-2-(2-methylpropyl)-3-oxo-5H-pyrido[3,4-b][1,4]benzothiazine-4-carbonitrile 10-oxide.

EXAMPLE 9

A mixture of 10 parts of 2,3-dihydro-3oxo-5H-pyrido[3,4-b][1,4]benzothiazine-4-carbonitrile, 45 parts of iodomethane, and 95 parts of N,N-dimethylformamide is heated at 100° for 2 hours, then diluted with 100 parts of water. The precipitate which forms is filtered out, dried in vacuo, and recrystallized from ethanol to give 2,3-dihydro-2,5-dimethyl-3-oxo-5H-pyrido[3,4-b][1,4]benzothiazine-4-carbonitrile melting at approximately 236°-237°.

EXAMPLE 10

A. A mixture of 3 parts of 5-chloro-2H-1,4-benzothiazin-3(4H)-one (J. Chem. Soc., 1945, 893), 1 part of diphosphorus pentasulfide, and 95 parts of 1,4-dioxane is stirred at the boiling point under reflux for 2½ hours, whereupon the mixture is allowed to cool to room temperature with continued stirring overnight. Liquid content is decanted from the solids present and diluted with 600 parts of water. The tan precipitate which forms is filtered off and dried at approximately 110°. The product thus isolated is 5-chloro-2H-1,4-benzothiazine-3(4H)-thione.

B. To 19 parts of sodium hydride and 1100 parts of tetrahydrofuran at room temperature under nitrogen is consecutively added, portionwise with stirring during approximately 30 minutes, 68 parts of 5-chloro-2H-1,4-benzothiazine-3(4H)-thione and 65 parts of iodomethane. Stirring at room temperature is continued for 30 minutes after the addition is complete, and the resultant solution of 5-chloro-3-methylthio-2H-1,4-benzothiazine is thereupon used as such a Part C of this example.

C. To 12 parts of sodium hydride in 760 parts of N,N-dimethylformamide at room temperature under nitrogen is added, portionwise with stirring during 30 minutes, 44 parts of 2-cyanoacetamide. A solution of 5-chloro-3-methylthio-2H-1,4-benzothiazine preparable as described in Part B of this example is then introduced; and the resultant mixture is heated to 70°, stirred thereat for 5½ hours, and finally allowed to cool to room temperature with continued stirring overnight, the nitrogen atmosphere having been maintained throughout. Upon addition of 3 volumes of water and adjustment of the pH to 5 with glacial acetic acid, precipitation occurs. The precipitate is separated by filtration, washed with ethyl acetate, then dried in vacuo. The substance thus isolated is 2-cyano-2-(5-chloro-2,3-dihydro-4H-benzothiazin-3-ylidene)-acetamide.

D. A mixture of 11 parts of 2-cyano-2-(5-chloro-2,3-dihydro-4H-benzothiazin-3-ylidene)acetamide, 8 parts of 1,1-diethoxy-N,N-dimethylmethanamine, and 20 parts of N,N-dimethylformamide is stirred at room temperature overnight, then heated to 145° and stirred thereat under reflux for 6 hours. The resultant mixture is allowed to cool to room temperature overnight, whereupon insoluble solids are filtered out, washed with ethyl acetate, then dried in vacuo at approximately 100°. The product thus isolated is 6-chloro-2,3-dihydro-3-oxo-5H-[3,4-b][1,4]-benzothiazine-4-carbonitrile.

EXAMPLE 11

A. Substitution of 3 parts of 6-fluoro-2H-1,4-benzothiazin-3(4H)-one (J. Chem. Soc., 1952, 787) for the 5-chloro-2H-1,4-benzothiazin-3(4H)-one called for in Example 10A affords, by the procedure there detailed, 6-fluoro-2H-1,4-benzothiazine-3(4H)-thione.

B. Substitution of 68 parts of 6-fluoro-2H-1,4-benzothiazine-3(4H)-thione for the 5-chloro-2H-1,4-benzothiazine-3(4H)-thione called for in Example 10B affords, by the procedure there detailed, 6-fluoro-3-methylthio-2H-1,4-benzothiazine.

C. Substitution of a solution of 6-fluoro-3-methylthio-2H-1,4-benzothiazine preparable as described in Part B of this example for the solution of 5-chloro-3-methylthio-2H-1,4-benzothiazine called for in Example 10C affords, by the procedure there detailed, 2-cyano-2-(6-fluoro-2,3-dihydro-4H-benzothiazin-3-ylidene)acetamide.

D. Substitution of 11 parts of 2-cyano-2-(6-fluoro-2,3-dihydro-4H-benzothiazin-3-ylidene)acetamide for the 2-cyano-2-(5-chloro-2,3-dihydro-4H-benzothiazin-3-ylidene)acetamide called for in Example 10D affords, by the procedure there detailed, 7-fluoro-2,3-dihydro-3-oxo-5H-pyrido[3,4-b][1,4]benzothiazine-4-carbonitrile.

EXAMPLE 12

A. Substitution of 3 parts of 6-chloro-2H-1,4-benzothiazin-3(4H)-one [Can. J. Chem., 44, 1733 (1965)] for the 5-chloro-2H-1,4-benzothiazin-3(4H)-one called for in Example 10A affords, by the procedure there detailed, 6-chloro-2H-1,4-benzothiazine-3(4H)-thione which, recrystallized from 95% ethanol, is obtained as peach-colored needles melting in the range, 205°–210°.

B. Substitution of 68 parts of 6-chloro-2H-1,4-benzothiazine-3(4H)-thione for the 5-chloro-2H-1,4-benzothiazine-3(4H)-thione called for in Example 10A affords, by the procedure there detailed, 6-chloro-3-methylthio-2H-1,4-benzothiazine.

C. Substitution of a solution of 6-chloro-3-methylthio-2H-1,4-benzothiazine preparable as described in Part B of this example for the solution of 5-chloro-3-methylthio-2H-1,4-benzothiazine called for in Example 10C affords, by the procedure there detailed, 2-cyano-2-(6-chloro-2,3-dihydro-4H-benzothiazin-3-ylidene)acetamide as small fluffy yellow needles melting with decomposition above 300°.

D. Substitution of 11 parts of 2-cyano-2-(6-chloro-2,3-dihydro-4H-benzothiazin-3-ylidene)acetamide for the 2-cyano-2-(5-chloro-2,3-dihydro-4H-benzothiazin-3-ylidene)acetamide called for in Example 10D affords, by the procedure there detailed, 7-chloro-2,3-dihydro-3-oxo-5H-pyrido[3,4-b][1,4]benzothiazine-4-carbonitrile which, recrystallized from aqueous N,N-dimethylformamide, is obtained as yellow needles melting above 300°.

EXAMPLE 13

A mixture of 1 part of 7-chloro-2,3-dihydro-3-oxo-5H-pyrido[3,4-b][1,4]benzothiazine-4-carbonitrile, 14 parts of ethaneperoxoic acid, and 58 parts of acetic acid is stirred at room temperature for 27 hours, whereupon insoluble solids are filtered out, dried in air, and recrystallized from aqueous N,N-dimethylformamide to give 7-chloro-2,3-dihydro-3-oxo-5H-pyrido[3,4-b][1,4]benzothiazine-4-carbonitrile 10-oxide as a colorless solid melting above 300°.

EXAMPLE 14

A mixture of 12 parts of 7-chloro-2,3-dihydro-3-oxo-5H-pyrido[3,4-b][1,4]benzothiazine-4-carbonitrile, 22 parts of ethaneperoxoic acid, and 445 parts of glacial acetic acid is stirred and heated at approximately 95° C., for 2½ hours, then cooled to room temperature. Insoluble solids are filtered out, washed with ethyl acetate, and dried in vacuo at 110° to give 7-chloro-2,3-dihydro-3-oxo-5H-pyrido[3,4-b][1,4]benzothiazine-4-carbonitrile 10,10-dioxide as off-white cottony needles melting above 300°.

EXAMPLE 15

A mixture of 60 parts of 2-cyano-2-(6-chloro-2,3-dihydro-4H-benzothiazin-3-ylidene)acetamide, 43 parts of 1,1-dimethoxy-N,N-dimethylethanamine, and 665 parts of N,N-dimethylformamide is stirred at room temperature overnight, then heated at 140°–150° for 5 hours, and finally allowed to cool to room temperature overnight, stirring being continued throughout. Insoluble solids are separated by filtration, washed with ethyl acetate, and dried in vacuo at 112° to give 7-chloro-1-methyl-2,3-dihydro-3-oxo-5H-pyrido[3,4-b][1,4]benzothiazine-4-carbonitrile as a bright yellow solid melting above 300°.

EXAMPLE 16

A. Substitution of 3 parts of 6-bromo-2H-1,4-benzothiazin-3(4H)-one (J. Chem. Soc., 1957, 2624) for the 5-chloro-2H-1,4-benzothiazin-3(4H)-one called for in Example 10A affords, by the procedure there detailed, 6-bromo-2H-1,4-benzothiazine-3(4H)-thione.

B. Substitution of 68 parts of 6-bromo-2H-1,4-benzothiazine-3(4H)-thione for the 5-chloro-2H-1,4-benzothiazine-3(4H)-thione called for in Example 10B affords, by the procedure there detailed, 6-bromo-3-methylthio-2H-1,4-benzothiazine.

C. Substitution of a solution of 6-bromo-3-methylthio-2H-1,4-benzothiazine preparable as described in Part B of this example for the solution of 5-chloro-3-methylthio-2H-1,4-benzothiazine called for in Example 10C affords, by the procedure there detailed, 2-cyano-2-(6-bromo-2,3-dihydro-4H-benzothiazine-3-ylidene)acetamide.

D. Substitution of 11 parts of 2-cyano-2-(6-bromo-2,3-dihydro-4H-benzothiazin-3-ylidene)acetamide for the 2-cyano-2-(5-chloro-2,3-dihydro-4H-benzothiazin-3-ylidene)-acetamide called for in Example 10D affords, by the procedure there detailed, 7-bromo-2,3-dihydro-3-oxo-5H-pyrido-[3,4-b][1,4]benzothiazine-4-carbonitrile.

EXAMPLE 17

A. A mixture of 21 parts of 7-chloro-2H-1,4-benzothiazin-3(4H)-one [Can. J. Chem., 48, 1859 (1970)], 10 parts of diphorphorus pentasulfide, and 565 parts of 1,4-dioxane is stirred at the boiling point under reflux for 3 hours. The resultant green solution is diluted with 3 volumes of water; and the pinkish-brown precipitate which forms is filtered out, dried in vacuo, recrystallized from ethanol, and dried by heating at 110° in vacuo to give 7-chloro-2H-1,4-benzothiazine-3(4H)-thione melting at 202°–204°.

B. To 18 parts of sodium hydride in 4000 parts of tetrahydrofuran at room temperature under nitrogen is consecutively added, portionwise with stirring, 129 parts of 7-chloro-2H-1,4-benzothiazine-3(4H)-thione and 123 parts of iodomethane. Stirring at room temperature is continued for 30 minutes after the addition is complete, and the resultant solution of 7-chloro-3-methylthio-2H-1,4-benzothiazine is thereupon used as such in Part C of this example.

C. To approximately 23 parts of sodium hydride in 4800 parts of N,N-dimethylformamide at room temperature under nitrogen is added, portionwise with stirring, 78 parts of 2-cyanoacetamide. Approximately 15 minutes later, a solution of 7-chloro-3-methylthio-2H-1,4-benzothiazine preparable as described in Part B of this example is slowly introduced, whereupon the reaction mixture is heated at 55° for 3 hours and then allowed to cool to room temperature overnight, stirring being continuous and the nitrogen atmosphere maintained throughout. The resultant mixture is acidified with glacial acetic acid and thereupon mixed with 3 volumes of water. Insoluble solids are filtered out and crystallized from aqueous N,N-dimethylformamide to give 2-cyano-2-(7-chloro-2,3-dihydro-4H-benzothiazin-3-ylidene)acetamide melting with decomposition in the range 150°–160°.

D. A mixture of 44 parts of 2-cyano-2-(7-chloro-2,3-dihydro-4H-benzothiazine-3-ylidene)acetamide, 29 parts of 1,1-diethoxy-N,N-dimethylmethanamine, and 570 parts of N,N-dimethylformamide is stirred at room temperature under nitrogen overnight, then heated to 140° and stirred thereat under reflux for 5½ hours. The resultant solution is concentrated to approximately ⅓ volume by vacuum distillation, and the concentrate is then cooled and thereupon diluted with sufficient ethyl acetate to induce incipient precipitation. When precipitation is essentially complete, the precipitate is filtered out, washed with ethyl acetate, dried in vacuo at 110°, crystallized from aqueous N,N-dimethylformamide, and again dried in vacuo at 110° to give 8-chloro-2,3-dihydro-3-oxo-5H-pyrido[3,4-b]-[1,4]benzothiazine-4-carbonitrile as small golden needles melting above 300°.

EXAMPLE 18

Substitution of 10 parts of 8-chloro-2,3-dihydro-3-oxo-5H-pyrido[3,4-b][1,4]benzothiazine-4-carbonitrile for the 2,3-dihydro-3-oxo-5H-pyrido[3,4-b][1,4]benzothiazine-4-carbonitrile called for in Example 2 affords, by the procedure there detailed, 8-chloro-2,3-dihydro-3-oxo-5H-pyrido[3,4-b][1,4]benzothiazine-4-carbonitrile 10-oxide.

EXAMPLE 19

A mixture of 21 parts of 8-chloro-2,3-dihydro-3-oxo-5H-pyrido[3,4-b][1,4]benzothiazine-4-carbonitrile, 56 parts of ethaneperoxoic acid, and 375 parts of glacial acetic acid is stirred and heated at 95° for 1 hour, whereupon insoluble solids are filtered out, washed with ethyl acetate, and dried in vacuo at 110° to give yellow 8-chloro-2,3-dihydro-3-oxo-5H-pyrido[3,4-b][1,4]benzothiazine-4-carbonitrile 10,10-dioxide melting above 300°.

EXAMPLE 20

To a solution of 20 parts of 2,3-dihydro-3-oxo-5H-pyrido[3,4-b][1,4]benzothiazine-4-carbonitrile in 1575 parts of glacial acetic acid is added a solution of 34 parts of bromine in 320 parts of carbon tetrachloride. The resultant mixture is heated at the boiling point under reflux for 2¾ hours, then chilled. The precipitate which forms is filtered off and recrystallized from N,N-dimethylformamide to give 8-bromo-2,3-dihydro-3-oxo-5H-pyrido[3,4-b][1,4]benzothiazine-4-carbonitrile melting above 305°.

EXAMPLE 21

A. Substitution of 3 parts of 5-nitro-2H-1,4-benzothiazin-3(4H)-one [Ann. Chim. (Rome), 58, 1226 (1968)] for the 5-chloro-2H-1,4-benzothiazin-3(4H)-one called for in Example 10A affords, by the procedure there detailed, 5-nitro-2H-1,4-benzothiazine-3(4H)-thione.

B. Substitution of 68 parts of 5-nitro-2H-1,4-benzothiazine-3(4H)-thione for the 5-chloro-2H-1,4-benzothiazine-3(4H)-thione called for in Example 10B affords, by the procedure there detailed, 3-methylthio-5-nitro-2H-1,4-benzothiazine.

C. Substitution of a solution of 3-methylthio-5-nitro-2H-1,4-benzothiazine preparable as described in Part B of this example for the solution of 5-chloro-3-methylthio-2H-1,4-benzothiazine called for in Example 10C affords, by the procedure there detailed, 2-cyano-2-(2,3-dihydro-5-nitro-4H-benzothiazin-3-ylidene)acetamide.

D. Substitution of 11 parts of 2-cyano-2-(2,3-dihydro-5-nitro-4H-benzothiazin-3-ylidene)acetamide for the 2-cyano-2-(5-chloro-2,3-dihydro-4H-benzothiazin-3-ylidene)acetamide called for in Example 10D affords, by the procedure there detailed, 2,3-dihydro-6-nitro-3-oxo-5H-pyrido[3,4-b][1,4]benzothiazine-4-carbonitrile.

EXAMPLE 22

To a solution of 5 parts of 2,3-dihydro-3-oxo-5H-pyrido[3,4-b][1,4]benzothiazine-4-carbonitrile in 90 parts of concentrated sulfuric acid at 0° is slowly added, with stirring, 7 parts of concentrated nitric acid. The resultant mixture is stirred at room temperature for 1 hour, whereupon 2 volumes of water is slowly stirred in. The light yellow precipitate which forms is filtered out and recrystallized from aqueous N,N-dimethylformamide to give needles of 2,3-dihydro-8-nitro-3-oxo-5H-pyrido[3,4-b][1,4]benzothiazine-4-carbonitrile 10-oxide solvated 1:1 with N,N-dimethylformamide which melts above 310°. The solvent of crystallization can be removed by prolonged heating at around 200° in vacuo.

EXAMPLE 23

To a solution of 27 parts of triphenylphosphine in a mixture of 195 parts of acetonitrile with 400 parts of carbon tetrachloride is added 12 parts of a 1:1 solvate of 2,3-dihydro-8-nitro-3-oxo-5H-pyrido[3,4-b][1,4]benzothiazine-4-carbonitrile 10-oxide with N,N-dimethylformamide. The resultant mixture is heated at the boiling point under reflux with stirring for 15 minutes, then chilled. The precipitate which forms is isolated by filtration and recrystallized from a mixture of N,N-dimethylformamide and methanol to give 2,3-dihydro-8-nitro-3-oxo-5H-pyrido[3,4-b][1,4]benzothiazine-4-carbonitrile solvated 2:1 with N,N-dimethylformamide which melts above 305°. The solvent of crystallization can be removed by heating at around 200° in vacuo.

EXAMPLE 24

To a suspension of 20 parts of 2,3-dihydro-6-nitro-3-oxo-5H-pyrido[3,4-b][1,4]benzothiazine-4-carbonitrile in 735 parts of glacial acetic acid is added a solution of 36 parts of stannous chloride dihydrate in 145 parts of concentrated hydrochloric acid. The resultant mixture is heated at the boiling point under reflux with stirring for 30 minutes, then chilled. Insoluble solids are filtered out, consecutively washed with glacial acetic acid and water, and dried by heating in vacuo at 100°. The product thus isolated is 6-amino-2,3-dihydro-3-oxo-5H-pyrido-[3,4-b][1,4]benzothiazine-4-carbonitrile hydrochloride.

EXAMPLE 25

To a suspension of 25 parts of a 1:1 solvate of 2,3-dihydro-8-nitro-3-oxo-5H-pyrido[3,4-b][1,4]benzothiazine-4-carbonitrile in 1000 parts of glacial acetic acid is added a solution of 75 parts of stannous chloride dihydrate in 230 parts of 28% hydrochloric acid. The resultant mixture is heated at the boiling point under reflux with stirring for 2 hours, then chilled. Insoluble solids are filtered out and dissolved in a mixture of 1100 parts of sulfinylbis[methane] with 200 parts of water. This solution is basified with concentrated ammonium hydroxide and thereupon diluted with 1 volume of water. The precipitate which forms is filtered off and consecutively recrystallized from (1) a mixture of sulfinylbis[methane] and methanol and (2) a mixture of sulfinylbis[methane], N,N-dimethylformamide, and water to give 8-amino-2,3-dihydro-3-oxo-5H-pyrido[3,4-b][1,4]benzothiazine-4-carbonitrile melting above 305°.

EXAMPLE 26

Substitution of 20 parts of a 2:1 solvate of 2,3-dihydro-8-nitro-3-oxo-5H-pyrido[3,4-b][1,4]benzothiazine-4-carbonitrile for the 2,3-dihydro-6-nitro-3-oxo-5H-[3,4-b][1,4]benzothiazine-4-carbonitrile called for in Example 24 affords, by the procedure there detailed, 8-amino-2,3-dihydro-3-amino-5H-pyrido[3,4-b][1,4]benzothiazine-4-carbonitrile hydrochloride which, rescrystallized from methanol and dried in vacuo, melts above 300°.

EXAMPLE 27

A. Substitution of 3 parts of 6,7-dimethoxy-2H-1,4-benzothiazin-3-(4H)-one (J. Proc. Roy. Soc., N.S. Wales, 71, 112 (1938) for the 5-chloro-2H-1,4-benzothiazin-3-(4H)-one called for in Example 10A affords, by the procedure there detailed, 6,7-dimethoxy-2H-1,4-benzothiazine-3(4H)-thione.

B. Substitution of 68 parts of 6,7-dimethoxy-2H-1,4-benzothiazine-3(4H)-thione for the 5-chloro-2H-1,4-benzothiazine-3(H)-thione called for in Example 10B affords, by the procedure there detailed, 6,7-dimethoxy-3-methylthio-2H-1,4-benzothiazine.

C. Substitution of a solution of 6,7-dimethoxy-3-methylthio-2H-1,4-benzothiazine preparable as described in Part B of this example for the solution of 5-chloro-3-methyl-thio-2H-1,4-benzothiazine called for in Example 10C affords, by the procedure there detailed, 2-cyano-2-(6,7-dimethoxy-2,3-dihydro-4H-benzothiazin-3-ylidene)acetamide.

D. Substitution of 11 parts of 2-cyano-2-(6,7-dimethoxy-2,3-dihydro-4H-benzothiazin-3-ylidene)acetamide for the 2-cyano-2-(5-chloro-2,3-dihydro-4H-benzothiazin-3-ylidene)acetamide called for in Example 10D affords, by the procedure there detailed, 7,8-dimethoxy-2,3-dihydro-3-oxo-5H-pyrido[3,4-b][1,4]benzothiazine-4-carbonitrile.

What is claimed is:

1. A compound of the formula

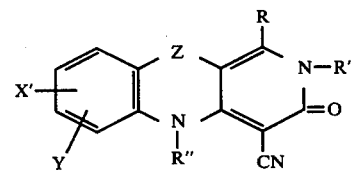

wherein R represents hydrogen or a straight-chain alkyl containing 1 to 3 carbon atoms; R' and R'' each represent hydrogen or straight-chain or branched-chain alkyl containing 1 to 3 carbon atoms; X' represents hydrogen, fluorine, chlorine, bromine, nitro, or straight-chain or branched-chain alkoxy containing 1 to 4 carbon atoms; when X' is other than alkoxy, Y represents hydrogen and, when X' is alkoxy, Y is hydrogen or the same alkoxy; and Z represents sulfur, sulfinyl, or sulfonyl.

2. A compound according to claim 1 wherein Z is sulfur.

3. A compound according to claim 2 wherein R, R'' X' and Y are hydrogen.

4. A compound according to claim 3 wherein R' is methyl.

5. A compound according to claim 3 wherein R' is hydrogen.

6. A compound according to claim 2 wherein R, R', and R'' are hydrogen.

7. A compound according to claim 6 wherein X' is fluorine, chlorine or bromine.

8. A compound according to claim 7 of the formula

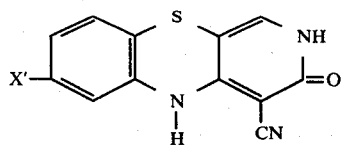

9. A compound according to claim 6 wherein X' is nitro.

10. A compound according to claim 6 wherein X' and Y are each methoxy.

11. A compound according to claim 10 of the formula

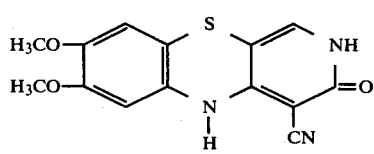

12. A compound according to claim 1 wherein Z is sulfinyl.

13. A compound according to claim 12 wherein R, R', R" and Y are hydrogen and X' is chlorine.

14. A compound according to claim 13 of the formula

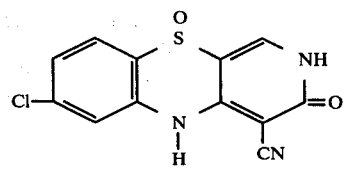

15. A compound according to claim 12 wherein R, R", X', and Y are hydrogen.

16. A compound according to claim 15 wherein R' is hydrogen.

17. A compound according to claim 1 wherein Z is sulfonyl.

18. A compound according to claim 17 wherein R, R', R" and Y are hydrogen and X' is chlorine.

19. A compound according to claim 18 of the formula

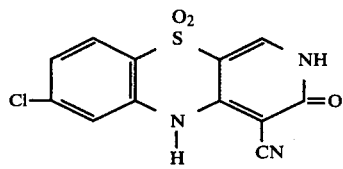

20. A compound according to claim 17 wherein R, R', R", X' and Y are hydrogen.

21. A compound of the formula

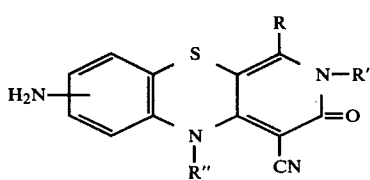

wherein R represents hydrogen or a straight-chain alkyl containing 1 to 3 carbon atoms and R' and R" each represent hydrogen or straight-chain or branched-chain alkyl containing 1 to 3 carbon atoms.

22. A compound according to claim 21 of the formula

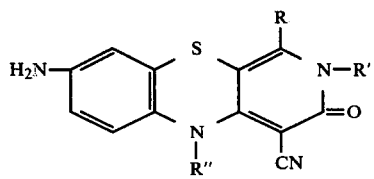

23. A compound according to claim 22 wherein R, R' and R" each represent hydrogen.

* * * * *